United States Patent
Catchpole (10) Patent No.: US 9,284,236 B2
(45) Date of Patent: Mar. 15, 2016

(54) APPARATUS AND PROCESS FOR TREATING NATURAL GAS

(75) Inventor: Stephen John Catchpole, Middlesbrough (GB)

(73) Assignee: Johnson Matthey PLC, London (GB)

( * ) Notice: Subject to any disclaimer, the term of this patent is extended or adjusted under 35 U.S.C. 154(b) by 897 days.

(21) Appl. No.: 13/520,442

(22) PCT Filed: Dec. 16, 2010

(86) PCT No.: PCT/GB2010/052115
§ 371 (c)(1),
(2), (4) Date: Dec. 21, 2012

(87) PCT Pub. No.: WO2011/083297
PCT Pub. Date: Jul. 14, 2011

(65) Prior Publication Data
US 2013/0090505 A1 Apr. 11, 2013

(30) Foreign Application Priority Data
Jan. 5, 2010 (GB) .................................. 1000097.4

(51) Int. Cl.
*C07C 5/00* (2006.01)
*C10L 3/08* (2006.01)
(Continued)

(52) U.S. Cl.
CPC ... *C07C 5/00* (2013.01); *B01J 8/00* (2013.01); *C10L 3/08* (2013.01); *C10L 3/10* (2013.01)

(58) Field of Classification Search
CPC .............. C01B 3/00; C01B 2203/1064; C01B 2203/1205
See application file for complete search history.

(56) References Cited

U.S. PATENT DOCUMENTS 3,744,981 A   7/1973   Ward
3,870,481 A   3/1975   Hegarty
(Continued)

FOREIGN PATENT DOCUMENTS

CN   1669909       9/2005
GB   2 432 369 A   5/2007
(Continued)

OTHER PUBLICATIONS

International Search Report dated Feb. 16, 2011, from PCT International Application No. PCT/GB2010/052115.
(Continued)

*Primary Examiner* — Matthew Merkling
(74) *Attorney, Agent, or Firm* — RatnerPrestia (57) ABSTRACT

A process is described for treating a natural gas stream containing methane and one or more higher hydrocarbons including the steps of:
(i) mixing at least a portion of the natural gas stream with steam,
(ii) passing the mixture adiabatically over a supported precious metal reforming catalyst to generate a reformed gas mixture comprising methane, steam, carbon dioxide, carbon monoxide and hydrogen,
(iii) cooling the reformed gas mixture to below the dew point to condense water and removing the condensate to provide a de-watered reformed gas mixture, and
(iv) passing the de-watered reformed gas mixture through an acid gas recovery unit to remove carbon dioxide and at least a portion of the hydrogen and carbon monoxide, thereby generating a methane stream.

The methane stream may be used to adjust the composition of a natural gas stream, including a vaporized LNG stream, to meet pipeline specifications.

20 Claims, 3 Drawing Sheets

(51) Int. Cl.
*C10L 3/10* (2006.01)
*B01J 8/00* (2006.01)

(56) References Cited

U.S. PATENT DOCUMENTS

| | | | | |
|---|---|---|---|---|
| 3,927,998 | A | * | 12/1975 | Child et al. ............... 48/197 R |
| 6,090,312 | A | | 7/2000 | Ziaka et al. |
| 6,564,579 | B1 | | 5/2003 | McCartney |
| 2005/0106428 | A1 | * | 5/2005 | Bolden ............... 429/19 |
| 2005/0207970 | A1 | | 9/2005 | Garg et al. |
| 2009/0158660 | A1 | | 6/2009 | Vanden Bussche et al. |
| 2010/0083830 | A1 | * | 4/2010 | Cross et al. ............... 95/134 |

FOREIGN PATENT DOCUMENTS

| | | |
|---|---|---|
| JP | 49-70901 | 7/1974 |
| JP | 11-49704 | 2/1999 |
| JP | 11-199878 | 7/1999 |
| JP | 11-199879 | 7/1999 |
| WO | WO-2010/004300 A1 | 1/2010 |

OTHER PUBLICATIONS

International Preliminary Report on Patentability dated Jul. 10, 2012, from PCT International Application No. PCT/GB2010/052115.
English Translation of Japanese Office Action for Japanese Patent Application 2012-546502 dated Mar. 26, 2015.

* cited by examiner

APPARATUS AND PROCESS FOR TREATING NATURAL GAS

CROSS-REFERENCE TO RELATED APPLICATIONS

This application is the U.S. National Phase application of PCT International Application No. PCT/GB2010/052115, filed Dec. 16, 2010, and claims priority of British Patent Application No. 1000097.4, filed Jan. 5, 2010, the disclosures of both of which are incorporated herein by reference in their entireties for all purposes.

FIELD OF THE INVENTION

This invention relates to a process for treating natural gas to remove higher hydrocarbons present therein to make it more suitable for liquefied natural gas (LNG) production or to adjust its composition to meet pipeline specifications.

BACKGROUND OF THE INVENTION

Natural gas, comprising methane and higher hydrocarbons such as ethane, propane and butane, is often recovered directly, or as an associated gas with oil production, offshore using fixed or floating platforms coupled to well heads on the seabed. The recovered natural gas is, where generally possible, fed via pipeline to on-shore gas processing facilities where such steps as purification may be carried out. For a significant proportion of the recovered natural gas, pipelining to on-shore facilities is not possible. In such cases it has become desirable to recover and liquefy the natural gas for sea transportation to on-shore facilities. Similarly, on-shore stranded natural gas is increasingly liquefied for transportation to overseas markets. The liquefaction processes typically include steps of cooling the natural gas to a very low temperature, which allows separation of at least some of the ethane, propane, butanes and other higher hydrocarbons from the methane. The liquefied products have different commercial values, but where further processing such as cracking is not feasible, typically the ethane has the lowest value, and so part is often used for power generation in the liquefaction facility and the excess is flared. Alternatively, in off shore production, the excess ethane may be recovered and transported alongside the LNG to the onshore facility. However the economics of transporting ethane in place of the more valuable liquids is less attractive. With ever-increasing pressure on maximising the utilisation of the recovered hydrocarbons coupled with a need to reduce flaring, which has become environmentally unsound, there is a need for an improved process for treating natural gas containing higher hydrocarbons.

Furthermore, so-called "rich" natural gas streams containing relatively large amounts of higher hydrocarbons, whether recovered directly or by vapourisation of rich-LNG's, often pose a problem for the processor required to meet pipeline specifications on their content and calorific value.

GB2432369 discloses a method of treating natural gas containing ethane based on the CRG process, developed originally by British Gas and licensed by Davy Process Technology Ltd. The method utilises a combination of adiabatic steam reforming over a nickel catalyst at temperatures in excess of 350° C., methanation and $CO_2$ removal on ethane extracted from the natural gas to generate methane, which is mixed with the natural gas, which may be liquefied.

This process has a number of drawbacks including the need to separate ethane and higher hydrocarbons as well as the methanation step, which is required to convert the carbon monoxide and hydrogen formed over the nickel catalyst back into methane.

Other processes are known for adjusting the calorific value of rich natural gases but these require the use of ballasting agents such as nitrogen, which has to be separately generated and stored.

SUMMARY OF THE INVENTION

We have developed a process that utilises the higher hydrocarbons in the natural gas to make methane and overcomes the problems of the previous natural gas treatment processes.

Accordingly the invention provides a process for treating a natural gas stream containing methane and one or more higher hydrocarbons comprising the steps of:
  (i) mixing at least a portion of the natural gas stream with steam,
  (ii) passing the mixture adiabatically over a supported precious metal reforming catalyst at an inlet temperature in the range 130-300° C. to generate a reformed gas mixture comprising methane, steam, carbon dioxide, carbon monoxide and hydrogen,
  (iii) cooling the reformed gas mixture to below the dew point to condense water and removing the condensate to provide a de-watered reformed gas mixture, and
  (iv) passing the de-watered reformed gas mixture through an acid gas recovery unit to remove carbon dioxide and at least a portion of the hydrogen and carbon monoxide, thereby generating a methane stream.

The methane stream may be used as a fuel or liquefied for transportation or storage. Alternatively the methane stream may be used to adjust the composition of a natural gas stream, including a vapourised LNG stream, to meet pipeline specifications.

By "higher hydrocarbons" we include one or more of ethane, propane, butanes and any C5+ paraffins, cycloalkanes such as cyclohexane, and aromatic hydrocarbons such as benzene.

By using a precious metal reforming catalyst, it is possible to include methane in the reformer feed, reduce the size of the reformer vessel and operate under conditions that remove the need for a methanation step. As a consequence, the weight is reduced and the footprint of the process is smaller which is particularly advantageous for off-shore operation of the process.

Accordingly the invention further provides apparatus for treating a natural gas stream containing methane and one or more higher hydrocarbons comprising:
  (i) means for adding steam to a natural gas stream,
  (ii) a reformer vessel operatively connected to the means for adding steam, said reformer vessel containing a supported precious metal reforming catalyst, configured such that the mixed natural gas stream and steam are passed over the catalyst to generate a reformed gas mixture comprising methane, steam, carbon dioxide, carbon monoxide and hydrogen,
  (iii) heat exchange means operatively connected to the reformer vessel to cool the reformed gas mixture to below the dew point and separation equipment operatively connected to the heat exchange means to recover process condensate and provide a de-watered reformed gas mixture, and
  (iv) an acid gas recovery unit operatively connected to the separation equipment to remove carbon dioxide and at least a portion of the hydrogen and carbon monoxide, thereby generating a methane stream.

The apparatus may further comprise natural gas liquefaction equipment operatively connected to the acid gas recovery unit to liquefy at least a portion of the methane stream. Alternatively or additionally the apparatus may further comprise mixing apparatus to combine the methane stream with a natural gas stream and/or higher hydrocarbon stream.

The process may be operated on-shore to overcome problems in existing rich natural gas liquefaction plants or may be used at LNG receiving terminals in re-gasification plants to adjust the composition of the vapourised LNG.

In a preferred embodiment the process is operated on an offshore natural gas processing facility. In this embodiment, natural gas is recovered and provided to an offshore natural gas processing facility using conventional recovery techniques and pipeline equipment. Preferably, the offshore natural gas processing facility is a fixed offshore facility or a floating offshore facility such as a floating liquefied natural gas production facility.

BRIEF DESCRIPTION OF THE DRAWINGS

The invention is further illustrated by reference to the figures in which.

DETAILED DESCRIPTION OF THE INVENTION

The natural gas stream treated according to the inventive method may be a natural gas, including associated gas, recovered from on-shore or off-shore reservoirs, or another gas mixture comprising methane and one or more higher hydrocarbons. Thus, whereas the natural gas stream may be natural gas itself, it may alternatively be a synthetic natural gas mixture comprising a mixture of methane or natural gas and one or more higher hydrocarbons that have been separated, e.g. by liquefaction, refrigeration or otherwise from a natural gas mixture. The natural gas stream may alternatively be a shale gas, tight sand gas or coal-bed methane gas. As well as methane and higher hydrocarbons, the natural gas may comprise carbon dioxide and/or nitrogen.

It is desirable that the amount of methane in the natural gas stream is in the range 5 to 99% by volume, preferably 25 to 95% more preferably 50 to 95% by volume as this allows the use of a saturator to give the desired steam:carbon ratio which overcomes the need for a separate steam drum while at the same time enabling a sufficiently high amount of higher hydrocarbon to be reformed. Using a saturator advantageous in terms of boiler fuel costs and in space, particularly where it is desired to operate the process offshore and it conveniently allows re-circulation of process condensate to the reforming step. Process condensate may contain soluble or partly soluble hydrocarbons and returning them to the reforming step is advantageous as a source of fuel and to reduce the water treatment/purification burden of the process.

In a preferred embodiment, the process further comprises a step of feeding at least a portion of the methane stream to a natural gas liquefaction plant. In one such embodiment, all the recovered natural gas is fed to the reforming process so that the natural gas liquefaction step processes only methane to LNG and no liquefied higher hydrocarbons (i.e. natural gas liquids) are produced. Such a process offers a considerable advantage over the current processes where fractionation and storage/flaring of natural gas liquids, such as ethane, propane and butane, are practised.

In an alternative embodiment, the reformer feed comprises a portion of the natural gas feed stream and the remaining portion is mixed with either the de-watered reformed gas mixture fed to the acid gas removal unit, or, where the $CO_2$ and $N_2$ contents of the recovered natural gas are low, directly with the methane stream itself. The portion of natural gas fed to the reformer in this case may be in the range 5-95% vol of the original natural gas feed stream. The relative proportions will depend on the amount of higher hydrocarbon required to be converted to methane. The product gas stream in this case is a methane-enriched natural gas stream. The methane enriched natural gas will contain reduced amounts of higher hydrocarbons. The methane-enriched natural gas stream may be transported by pipeline to be used as a fuel for industrial or domestic purposes or may be liquefied using conventional LNG liquefaction and fractionation equipment to provide a LNG stream and one or more higher hydrocarbon streams. By removing a portion of the higher hydrocarbons from the feed to the liquefaction and fractionation plant, its size and operating costs may be reduced. One or more of the higher hydrocarbon streams separated in the liquefaction may be used as fuels or chemical feedstocks, or fed to the reformer as part of the natural gas stream.

In a further embodiment that includes a natural gas liquefaction step, a natural gas feedstock is mixed with the de-watered reformed gas mixture and the resulting mixture fed to the acid gas recovery unit to generate a methane-enriched natural gas stream, a portion of which is mixed with one or more higher hydrocarbons to generate a synthetic natural gas stream for the reforming stage. The remaining portion of the methane-enriched natural gas stream is fed to a natural gas liquefaction and fractionation unit that separates higher hydrocarbons, one or more of which are included in the natural gas stream fed to the reformer. The portion of the methane-enriched natural gas forming the synthetic natural gas stream fed to the reformer in this case may be in the range 5-95% vol.

The process of the present invention is desirably operated at pressures in the range 10-100 bar abs, preferably in the range 10-50 bar abs, which may be achieved by compression of the natural gas stream, where necessary.

The natural gas stream is desirably preheated prior to admixture with steam and the reforming step using conventional means such as a fired heater, which may also be used to generate the steam subsequently mixed with the natural gas stream, or by exchanging heat with the reformed gas mixture. The natural gas stream is desirably heated to a temperature in the range 75-275° C., preferably 100-220° C. prior to mixing with steam.

Where the natural gas contains mercury, it may be desirable to include a step of purifying the natural gas to remove mercury. Removing mercury protects process operators and equipment. For example, removing mercury upstream of liquefaction protects the heat exchangers, which are often fabricated from aluminium, from the corrosive effect of mercury. Thus, preferably, the process comprises passing the natural gas over a mercury sorbent disposed in a purification vessel. Desirably this unit is installed upstream of the means for adding steam in order to prevent mercury from contaminating the reforming process. Suitable mercury sorbents include transition metal sulphides, particularly copper sulphide, mixed with various support materials in the form of agglomerates. Such materials are commercially available from Johnson Matthey PLC, for example as PURASPEC$_{JM}$™ 1163. Alternatively, a transition metal compound, e.g. copper hydroxycarbonate, may be provided in a suitable form to the unit and sulphided in-situ by sulphur compounds present in the natural gas, thereby resulting in co-removal of sulphur and mercury. The mercury removal step is preferably operated below 150° C., more preferably below 100° C., and at pressures up to about 200 bar abs, e.g. in the range 10-100 bar abs. Accordingly, a mercury removal stage may be included before or after any stage of heating the natural gas stream. Where the natural gas contains sulphur compounds, it may be desirable that the process further comprises a step purifying the natural gas stream to remove sulphur compounds upstream of the reforming step in order to protect the reforming catalyst from the poisoning effect of sulphur. Thus, the process may comprise the step of desulphurising the natural gas stream by passing it over one or more desulphurisation materials disposed in a desulphuriser vessel. The desulphurisation of the natural gas stream is preferably carried out upstream of the reformer vessel, more preferably upstream of the means for adding steam. The sulphur compounds may include one or more of hydrogen sulphide ($H_2S$), carbonyl sulphide (COS), mercaptans, sulphides, and thiophenes. $H_2S$ may simply be absorbed using one or more beds of sulphur absorbent such as a commercially available ZnO or a metal-promoted, e.g. Cu-promoted, ZnO/alumina composition, at temperatures in the range 50-275° C. Where sulphur compounds other than hydrogen sulphide are present in high concentrations, it may be desirable to include a first step of hydrodesulphurisation followed by a step of hydrogen sulphide absorption. In this embodiment, the desulphurisation materials comprise a bed of hydrodesulphurisation catalyst located upstream of a bed of hydrogen sulphide absorbent. In hydrodesulphurisation, the natural gas stream containing a small amount, e.g. 1-2% vol, of hydrogen are passed over a Ni- and/or Co-based catalyst that converts the organo-sulphur compounds to hydrogen sulphide. Typical catalysts are alumina-supported Ni/Mo, Co/Mo, Ni/W, and Co/W catalysts. Such catalysts are available commercially. The hydrogen sulphide thus generated, in addition to any hydrogen sulphide naturally present in the natural gas, may then be absorbed by a suitable hydrogen sulphide absorbent, such as a ZnO-material. Again, such absorbent materials are available commercially. The hydrodesulphurisation catalyst may also be effective for hydrogenating olefins and converting amines to ammonia. The hydrodesulphurisation catalyst and hydrogen sulphide absorbent may be in the same or different vessels. The combined hydrodesulphurisation and $H_2S$ absorption is preferably operated above 150° C., more preferably above 200° C., and at pressures up to about 100 bar abs. Hydrogen required for hydrodesulphurisation may be provided from storage, a separate hydrogen generator apparatus, or by recycling a portion of the de-watered reformed gas mixture.

Where the precious metal reforming catalyst is sulphur-resistant, the sulphur compounds, particularly hydrogen sulphide, may instead be removed alongside carbon dioxide in the acid gas recovery unit using a membrane, a physical wash solvent or an aqueous amine.

The natural gas stream after any compression, heating and purification stages is then mixed with steam. This may be by direct injection of steam from a conventional steam drum but is preferably by means of one or more saturators. Alternatively a combination of direct steam addition and a saturator may be used. In a saturator, the natural gas stream is contacted with a re-circulated stream of pressurised hot water at temperatures typically >160° C. In order to increase the efficiency, the saturator desirably contains a packed bed of ceramic rings or other suitable packing media. The steam:carbon ratio in the reformer feed should be controlled to avoid carbon deposition on the catalyst. One advantage of using precious metal reforming catalysts compared to nickel reforming catalysts, is their greater resistance to carbon formation at low steam:carbon ratios. In addition, the lower thermal mass required with precious metal catalysts also offers a faster start-up than conventional nickel-catalysed reforming processes. Because, in the present invention, the methane is largely inert in the reforming stage the steam:carbon ratio may be in the range 0.2 to 3:1, preferably in the range 1 to 2.5:1, based on the higher hydrocarbon carbon.

In a preferred embodiment, a portion of the steam mixed with the natural gas stream is generated from at least a portion of the recovered condensate. Thus, preferably the separation equipment is operatively connected to the means for adding steam to the natural gas stream so that at least a portion of the recovered condensate is used to generate at least a portion of the steam mixed with the natural gas stream.

A further source of water for steam reforming may be molecular sieve or glycol driers that can be used to dry the methane stream or methane-enriched natural gas stream prior to liquefaction.

The temperature of the natural gas stream/steam mixture may be controlled for example using the preheater and/or steam temperature, and is in the range 130-300° C., but is preferably 150-275° C., more preferably 160-200° C., e.g. 200-220° C. at the inlet of the reformer vessel.

The pressure of the natural gas/steam mixture fed to the reforming catalyst is preferably in the range 10-100 bar abs.

Preferably, hydrogen is included, at least temporarily, in the reformer feed at concentrations up to 5% vol, more preferably at concentrations up to 3% vol, most preferably 1-2% vol. This may be achieved by feeding hydrogen to the natural gas stream and/or hydrocarbon/steam mixture upstream of the reformer. Thus hydrogen may be added to the natural gas stream upstream of any hydrodesulphurisation or saturator and/or, if desired, added to the hydrocarbon steam mixture upstream of the reformer. The hydrogen may be sourced from bottled supplies or may be generated electrolytically from water, or by steam reforming a separated natural gas stream or a separated reformed gas stream using a small-scale adiabatic reformer containing nickel catalysts.

In this case, a minor portion of the purified hydrocarbon stream or reformed gas mixture, which comprise methane, may be mixed with steam and the mixture heated in the fired heater and passed through the adiabatic steam reformer unit containing the catalyst at temperatures in the range 350-500° C. to generate a reformed gas mixture containing sufficient hydrogen for the reformer feed stream. Alternatively or additionally, a portion of the reformed gas mixture, which contains a small amount of hydrogen, may be re-circulated to the reformer.

The mixture comprising the natural gas stream and steam, and any hydrogen, is passed to a reformer vessel containing a supported precious metal reforming catalyst. Reforming reactions take place adiabatically over the precious metal catalyst to convert the higher hydrocarbons present to methane with only a small amount of methane converted to carbon oxides, hydrogen and steam. The reforming catalyst is a supported precious metal catalyst. Suitable catalysts comprise one or more of Pt, Pd, Ir, Rh or Ru, preferably Rh or Ru. Especially preferred catalysts comprise Ru, on a catalyst support, optionally with one or more promoters. Ru catalysts, particularly promoted Ru catalysts, can operate at higher space velocities, lower steam ratios and lower temperatures than conventional Ni steam reforming catalysts. Precious metal loading on the support may be in the range 0.1-10.0% wt, but is preferably 0.5-5% by weight. The catalyst support may be any conventional catalyst support suitable for operation in steam reformers such as alumina, calcium aluminate, magnesia, titania, zirconia or other refractory oxide materials. As the reforming temperature is relatively low, high surface area supports may be advantageously used such as transition aluminas including gamma-, delta- or theta-aluminas. The reforming catalyst may be in the form of shaped units such as rings or cylinders with one or more through-holes and/or one or more flutes or grooves running along the length of the unit. Such shaped units offer high geometric surface areas combined with low pressure drop. Alternatively the catalyst may be in the form of a monolith, i.e. a honeycomb, formed from a metal or ceramic substrate onto which a washcoat containing the precious metal has been coated. Suitable catalysts may be prepared by conventional methods such as by impregnating the support with a soluble salt of precious metal or my preparing a washcoat containing a suitable precious metal compound and coating the support with the washcoat, followed by drying calcination and, if desired, reduction of the metal to its active form. Reduction of the metal may if desired be performed in-situ, in which case the catalyst may be provided in oxidic form.

Hence, the reforming step may be operated at a pressure in the range 10 to 70 bar, preferably 10 to 50 bar, and an inlet temperature in the range 160 to 220° C., preferably 160-200° C., over a supported Ruthenium catalyst.

The reformed gas mixture comprising methane and steam with some carbon dioxide, carbon monoxide and hydrogen is then cooled using one or more heat exchangers, which may advantageously be used to preheat the steam used in the reforming step and/or used to provide heat for the acid-gas recovery unit where physical- and chemical-wash solvents are employed. The cooling is continued to below the dew point to condense the steam.

The cooled gas/condensate mixture is then passed to separation equipment preferably comprising one or more separators, more preferably with further cooling, to collect and recover process condensate. As stated above, the process condensate is a valuable source of water and may be used to generate a portion of the steam that is mixed with the natural gas stream. The gaseous product from the separation stage is a de-watered reformed gas mixture comprising methane with some carbon dioxide and minor amounts of carbon monoxide and hydrogen. In order that the acid gas recovery unit is able to efficiently remove the reforming by-products, the de-watered reformed gas mixture preferably contains ≤5% vol, preferably ≤3% vol, more preferably ≤1% vol $H_2$. The CO content of the de-watered reformed gas is preferably ≤1% vol, preferably ≤0.5% vol, more preferably ≤0.1% vol. The $CO_2$ content of the de-watered reformed gas may be in the range 5-25% vol.

Carbon dioxide is undesirable in the methane product stream because it can alter the calorific value of the natural gas and freezes above the natural gas liquefaction temperatures. Therefore, the present invention includes a step of passing the de-watered reformed gas mixture, which may further comprise a portion of natural gas, through an acid gas recovery unit (AGRU). Such AGRUs are currently used at the front end of LNG plants. Acid-gas removal, may be accomplished using membrane technology (e.g. based on anisotropic cellulose acetate, polyimide or perfluoropolymer membranes) or the known aqueous chemical wash (e.g. amine wash) or physical wash processes that use solvents such as cold methanol, N-methyl pyrrolidone or propylene carbonate, or glycol ether. Where physical wash solvents are used, it is desirable to dry the dewatered reformed gas mixture before passing it to the AGRU using conventional zeolite or glycol drying steps. Amine wash processes, which are commercially available, are preferred.

The AGRU removes the carbon dioxide and at least a portion of the carbon monoxide and hydrogen present in the de-watered reformed gas giving a methane stream, or where natural gas is mixed with the de-watered reformed gas, a methane-enriched natural gas stream.

Where the acid gas recovery unit utilizes a solvent or amine wash, suitable protection means such as a sorbent bed are desirably provided downstream to prevent contamination of downstream processes with these fluids.

The product methane stream may be further dried and compressed for pipeline distribution using conventional equipment, or it may be mixed with a natural gas stream and processed conventionally to provide a fuel for domestic or industrial use.

In one embodiment of the present invention, at least a portion of the methane stream or methane-enriched natural gas stream is cooled and liquefied to generate a methane-enriched LNG. Higher hydrocarbon fractions so-produced may be commercialised as fuels or as chemical feedstocks or may be returned to the reforming process as part of the natural gas stream.

Where the methane stream or methane-enriched natural gas stream is fed to a natural gas liquefaction plant, it is preferably subjected to one or more drying stages to prevent any entrained water vapour from freezing in the liquefaction equipment. Furthermore, removal of water vapour is desirable in order to avoid the formation of hydrocarbon hydrates in the gas stream and also to avoid the water condensing out of the gas in pipelines and process equipment which may then lead to corrosion problems. The drying step may be accomplished using known methods for drying natural gas mixtures, such as by contacting the gas with a bed of a solid desiccant such as a silica gel or molecular sieve, or the use of liquid desiccant compounds, such as glycols. In order to reach the very low water levels required for efficient operation of the liquefaction unit, molecular sieve driers containing, e.g. zeolites, are preferred. After drying, the dried methane stream or dried methane-enriched natural gas stream may be passed to a liquefaction unit to generate a liquefied natural gas stream. The water recovered from the molecular sieve or glycol driers upon their regeneration may usefully be fed to the process as a source of steam.

Where a methane-enriched natural gas is fed to a liquefaction process, it may be desirable to subject the natural gas, before it is mixed with the methane stream, to one or more steps of mercury and/or sulphur compound removal as described above to remove any mercury and sulphur compounds that may be present to prevent contamination of the AGRU and downstream equipment.

The liquefaction unit desirably comprises a natural gas liquefaction unit and optionally one or more fractionation columns depending upon the composition of the methane-containing stream.

Preferably, the dried methane stream or dried methane enriched natural gas stream is fed to a liquefaction unit where it is cooled firstly to between −20 and −40° C. before being fed to a first fractionation column where the heavy hydrocarbons are separated from a methane-rich stream. The light fraction from the top of the column is further cooled and condensed liquids separated. Thus the higher hydrocarbons are liquefied. One or more further columns may be used on the light and heavy fractions from the first column to obtain fractions rich in methane, ethane, propane, butanes and other hydrocarbons. Methods for processing the liquefied natural gas streams in this way are described for example in U.S. Pat. No. 6,564,579.

Where the feed to the liquefaction unit consists of a methane stream, no fractionation to produce natural gas liquids is required.

Where the feed to the liquefaction unit comprises a methane-enriched natural gas stream, desirably the liquefaction unit is operated such that a methane-enriched natural gas stream is separated into a methane-rich stream (i.e. a liquefied natural gas), an ethane stream, an LPG stream (containing propane and butanes) and a heavy stream.

The higher hydrocarbons that may be fed to the reforming step preferably comprises ethane and optionally a portion of the LPG and/or a heavy stream containing C5+ paraffins. Preferably >50% by volume, preferably >75%, more preferably >90% of the higher hydrocarbons fed to the reforming step is ethane.

Ethane, propane butane and other higher hydrocarbons not used in reforming may be used to generate power for the process, e.g. using a gas turbine.

The present invention, by converting the higher hydrocarbons to methane, provides a gas stream suitable for adjusting rich natural gas compositions to meet pipeline specifications and in particular, when combined with natural gas liquefaction, overcomes the problem of flaring and/or storing & transporting higher hydrocarbons and increases LNG production. Removing or reducing LPG storage also improves the safety of the natural gas liquefaction and storage facility. Moreover, removing higher hydrocarbons with relatively high melting points, particularly C5+ hydrocarbons, overcomes problems such as blockages in the liquefaction plant caused by freezing and foaming in the acid gas removal unit.

Figure 1:
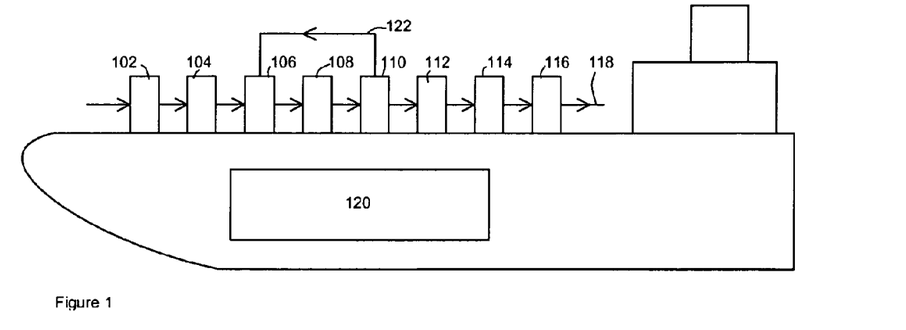
FIG. 1 depicts an arrangement of unit operations for a first embodiment of the present invention on an a floating liquid natural gas-production unit configured to process a rich natural gas into a LNG stream.

In FIG. 1 a floating LNG production unit 100 has mounted thereon and operatively connected to each other a mercury removal unit 102 fed with natural gas, a desulphurisation unit 104, a saturator 106 for adding steam to the desulphurised natural gas, a reformer vessel 108, heat exchange and process condensate separation equipment 110, an acid gas removal unit 112, a gas drying unit 114, and liquefaction equipment 116, that produces a liquefied natural gas stream 118 for storage in storage tanks 120. Process condensate recovered from the separation equipment 110 is fed via line 122 to the saturator 106 to generate a portion of the steam.

Figure 2:
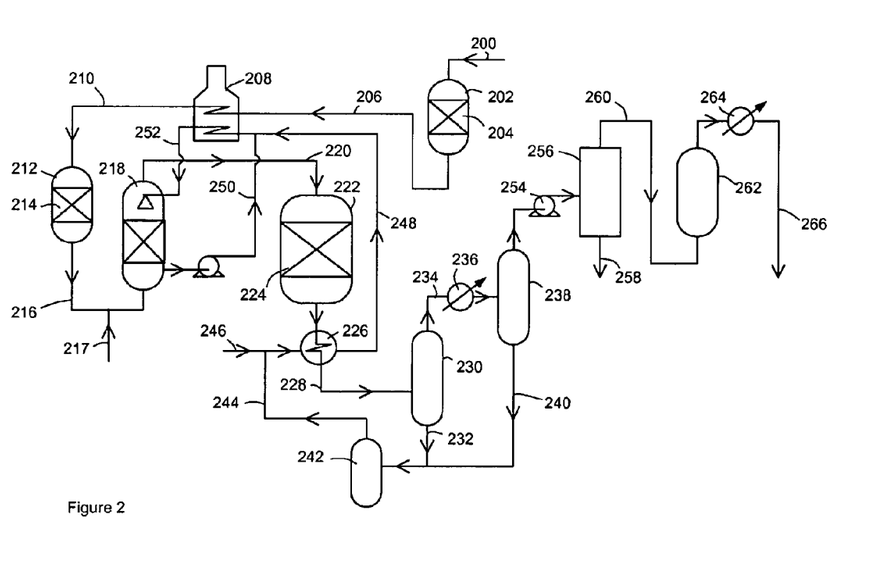
FIG. 2 is a flowsheet depicting a process according to the first embodiment.

In FIG. 2, a natural gas feed stream 200 is passed at a temperature below 100° C. and a pressure of about 10 bar abs, to a first purification vessel 202 containing a particulate copper-sulphide based mercury absorbent 204. Mercury and other heavy metals such as arsenic are absorbed by the absorbent. The resulting gas stream 206 is fed though coils in a fired heater 208 fuelled by natural gas and/or higher hydrocarbon, where it is heated to a temperature about 110° C. From fired heater 208 the gas is passed via line 210 to a desulphuriser vessel 212 containing a fixed bed of a particulate zinc oxide desulphurisation absorbent 214 that removes hydrogen sulphide present in the gas. The desulphurised natural gas stream is passed from the desulphuriser vessel 212 via line 216, mixed with a hydrogen stream in line 217 and the mixture fed to a saturator 218 where it is contacted with a stream of hot water/steam at a temperature about 190° C. at a pressure about 10 bar abs. The saturated hydrocarbon/steam mixture is then fed at a temperature about 180° C. via line 220 to the inlet of a reformer vessel 222 containing a supported ruthenium steam reforming catalyst 224. The steam reforming reactions take place adiabatically as the hydrocarbon-steam mixture passes through the catalyst 224. The hot reformed gas mixture is cooled in a heat exchanger 226 and one or more further heat exchangers (not shown) to below the dew point to generate a condensate/gas mixture, which is fed via line 228 to a first separator 230. The condensed liquids are recovered via line 232 and the gases fed via line 234 to a water-cooled heat exchanger 236 where they are further cooled, and then to a second separator 238. The remaining condensate is recovered from the separator 238 via line 240 and combined with the condensate stream 232 from the first separator.

The combined condensate streams are fed to a condensate stripper 242. A water feed stream 244 from the condensate stripper is mixed with make-up boiler feed water 246 and the combined water fed to the heat exchanger 226 where it is heated in indirect heat exchange with the reformed gas mixture. A heated water/steam stream 248 from the heat exchanger 226 is combined with a pumped re-circulated hot water stream 250 from the saturator 218 and the combined water/steam mixture is further heated by passing it through coils in the fired heater 208. The heated water/steam stream is then fed to the saturator 218 from the fired heater 208 via line 252.

The de-watered reformed gas mixture recovered from the second separator 238 is fed via pump 254 to acid gas recovery unit (AGRU) 256. The acid-gas removal unit 256 contains a membrane that separates $CO_2$, and at least part of the hydrogen and CO from the gas stream. The $CO_2$-rich stream is recovered from the AGRU via line 258 In an alternative embodiment, the acid-gas removal step uses an amine wash unit that removes the $CO_2$ and some $H_2S$ by contacting the gas with an aqueous amine solution. In yet a further alternative embodiment, the acid-gas removal step uses a physical wash solvent unit that removes the $CO_2$ and some $H_2S$ by contacting the gas with refrigerated methanol, glycol, N-methyl pyrrolidone, or propylene carbonate.

The resulting methane gas stream is fed from the AGRU 256 via line 260 to a drier vessel 262 where it contacts a zeolitic molecular sieve that acts as a desiccant to remove water. The dried methane gas stream is then cooled to between −20 and −40° C. in one or more heat exchangers 264 to form a liquefied natural gas stream 266.

Figure 3:
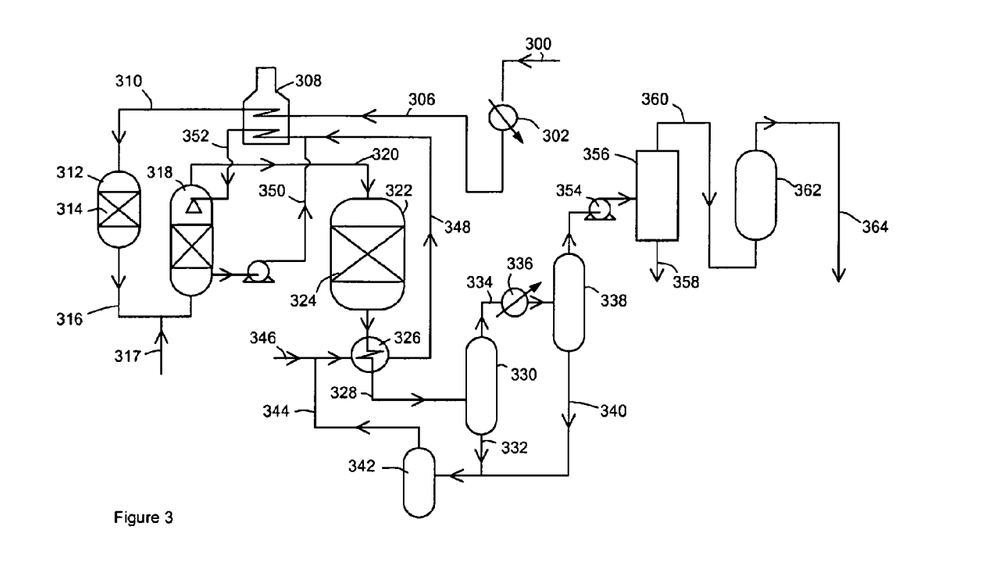
FIG. 3 is a flowsheet depicting a process according to a second embodiment configured to process a rich-LNG stream into a methane stream.

In FIG. 3, a liquefied natural gas feed stream 300 is passed through vapouriser 302 to form a rich natural gas stream. The vapourised gas stream 306 is fed though coils in a fired heater 308 fuelled by natural gas and/or higher hydrocarbon, where it is heated to a temperature about 110° C. From fired heater 308 the gas is passed via line 310 to a desulphuriser vessel 312 containing a fixed bed of a particulate zinc oxide desulphurisation absorbent 314 that removes hydrogen sulphide present in the gas. The desulphurised natural gas stream is passed from the desulphuriser vessel 312 vial line 316, mixed with a hydrogen stream in line 317 and the mixture fed to a saturator 318 where it is contacted with a stream of hot water/steam at a temperature about 190° C. at a pressure about 10 bar abs. The saturated hydrocarbon/steam mixture is then fed at a temperature about 180° C. via line 320 to the inlet of a reformer vessel 322 containing a supported ruthenium steam reforming catalyst 324. The steam reforming reactions take place adiabatically as the hydrocarbon-steam mixture passes through the catalyst 324. The hot reformed gas mixture is cooled in a heat exchanger 326 and one or more further heat exchangers (not shown) to below the dew point to generate a condensate/gas mixture, which is fed via line 328 to a first separator 330. The condensed liquids are recovered via line 332 and the gases fed via line 334 to a water-cooled heat exchanger 336 where they are further cooled, and then to a second separator 338. The remaining condensate is recovered from the separator 338 via line 340 and combined with the condensate stream 332 from the first separator.

The combined condensate streams are fed to a condensate stripper 342. A water feed stream 344 from the condensate stripper is mixed with make-up boiler feed water 346 and the combined water fed to the heat exchanger 326 where it is heated in indirect heat exchange with the reformed gas mixture. A heated water/steam stream 348 from the heat exchanger 326 is combined with a pumped re-circulated hot water stream 350 from the saturator 318 and the combined water/steam mixture is further heated by passing it through coils in the fired heater 308. The heated water/steam stream is then fed to the saturator 318 from the fired heater 308 via line 352.

The de-watered reformed gas mixture recovered from the second separator 338 is fed via pump 354 to acid gas recovery unit (AGRU) 356. The acid-gas removal unit 356 contains a membrane that separates $CO_2$, and at least part of the hydrogen and CO from the gas stream. The $CO_2$-rich stream is recovered from the AGRU via line 358 In an alternative embodiment, the acid-gas removal step uses an amine wash unit that removes the $CO_2$ and some $H_2S$ by contacting the gas with an aqueous amine solution. In yet a further alternative embodiment, the acid-gas removal step uses a physical wash solvent unit that removes the $CO_2$ and some $H_2S$ by contacting the gas with refrigerated methanol, glycol, N-methyl pyrrolidone or propylene carbonate.

The resulting methane gas stream is fed from the AGRU 356 via line 360 to a drier vessel 362 where it contacts a zeolitic molecular sieve that acts as a desiccant to remove water. The dried methane gas stream is then recovered from the drier 362 via line 364. The dried gas may be used as a fuel directly or combined with a natural gas stream to adjust the latter's composition and calorific value.

Figure 4:
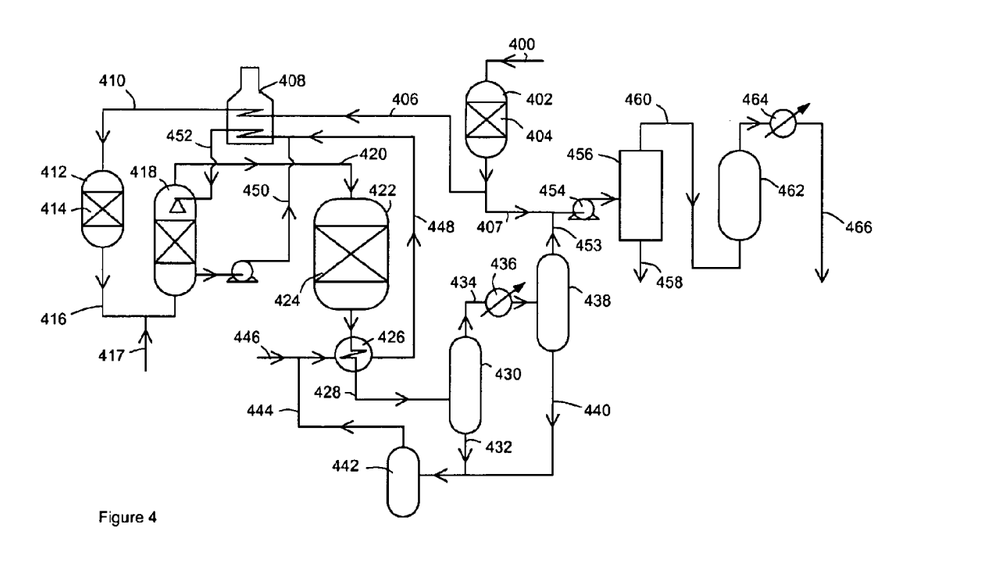
FIG. 4 is a flowsheet depicting a process according to a third embodiment configured to convert a rich natural gas into a LNG stream and one or more higher hydrocarbon streams.

In FIG. 4, a natural gas feed stream 400 is passed at a temperature below 100° C. and a pressure of about 10 bar abs, to a first purification vessel 402 containing a particulate copper-sulphide based mercury absorbent 404. Mercury and other heavy metals such as arsenic are absorbed by the absorbent. The resulting gas stream is divided into two streams; a first stream 406 and a second stream 407. The first stream 406 is fed though coils in a fired heater 408 fuelled by natural gas and/or higher hydrocarbon, where it is heated to a temperature about 110° C. From fired heater 408 the gas is passed via line 410 to a desulphurisation vessel 412 containing a fixed bed of a particulate zinc oxide desulphurisation absorbent 414 that removes hydrogen sulphide present in the gas. The desulphurised natural gas stream is passed from the desulphurisation vessel 412 via line 416, mixed with a hydrogen stream in line 417, and the mixture fed to a saturator 418 where it is contacted with a stream of hot water/steam at a temperature about 190° C. and a pressure about 10 bar abs. The saturated hydrocarbon/steam mixture is then fed at a temperature about 180° C. via line 420 to the inlet of a reformer vessel 422 containing a supported ruthenium steam reforming catalyst 424. The steam reforming reactions take place adiabatically as the hydrocarbon-steam mixture passes through the catalyst. The hot reformed gas mixture exits the reformer 422, is cooled in a heat exchanger 426 and one or more further heat exchangers (not shown) to below the dew point to generate a condensate/gas mixture, which is fed via line 428 to a first separator 430. The condensed liquids are recovered via line 432 and the gases fed via line 434 to a water-cooled heat exchanger 436 where they are further cooled before being passed to a second separator 438. The remaining condensate is recovered from the separator 438 via line 440 and combined with the condensate stream 432 from the first separator.

The combined condensate streams are fed to a condensate stripper 442. A water feed stream 444 from the condensate stripper is mixed with make-up boiler feed water 446 and the combined water fed to the heat exchanger 426 where it is heated by the reformed gas mixture. A heated water/steam stream 448 from the heat exchanger 426 is combined with a pumped re-circulated hot water stream 450 from the saturator 418 and the combined water/steam mixture is further heated by passing it through coils in the fired heater 408. The heated water/steam stream is fed to the saturator 418 from the fired heater 408 via line 452.

The de-watered reformed gas mixture 453 recovered from the second separator 438 is combined with the second stream of purified natural gas 407 and fed via pump 454 to an acid gas recovery unit (AGRU) 456. The acid-gas removal unit 456, contains a suitable membrane that separates carbon dioxide, and at least part of the hydrogen and carbon monoxide from the gas stream. A carbon monoxide-rich stream is recovered from the AGRU via line 458. In an alternative embodiment, the acid-gas removal step uses an amine wash unit that removes the carbon dioxide, hydrogen, carbon monoxide and some hydrogen sulphide by contacting the gas with an aqueous amine solution. In yet a further alternative embodiment, the acid-gas removal step uses a physical wash solvent unit that removes the carbon dioxide, hydrogen, carbon monoxide and some hydrogen sulphide by contacting the gas with refrigerated methanol, glycol, N-methyl pyrrolidone, or propylene carbonate.

The resulting methane-enriched natural gas stream is fed from the AGRU 456 via line 460 to a drier vessel 462 where it contacts a zeolitic molecular sieve that acts as a desiccant to remove water. The dried gas stream is then cooled to between −20 and −40° C. in one or more heat exchangers 464 to form a liquefied natural gas stream 466, which is fractionated to produce ethane-, propane- and butane-rich streams. If desired, at least a portion of the ethane stream may be vapourised and fed to line 406 (not shown).

Figure 5:
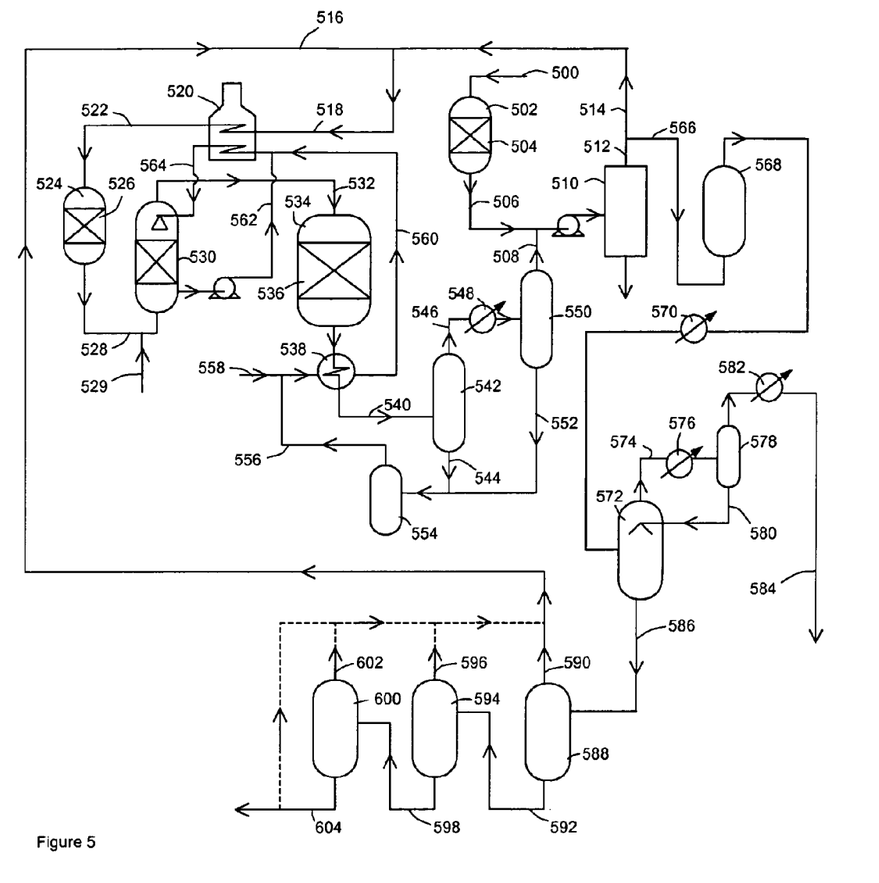
FIG. 5 is a flowsheet depicting a process according to a further embodiment configured to convert a rich natural gas into a LNG stream and one or more higher hydrocarbon streams.

In FIG. 5, a natural gas feed stream 500 is passed at a temperature below 100° C. and a pressure in the range 10-100 bar abs, e.g. about 10 bar abs, to a first purification vessel 502 containing a particulate copper-sulphide based mercury absorbent 504. Mercury and other heavy metals such as arsenic are absorbed by the absorbent. The resulting purified natural gas stream 506 is mixed with a de-watered reformed gas stream 508 and the resulting gas stream fed to an acid-gas removal vessel 510, containing a suitable membrane that separates $CO_2$ from the gas stream. In an alternative embodiment, the acid-gas removal step uses an amine wash unit that removes the $CO_2$ and some $H_2S$ by contacting the gas with an aqueous amine solution. In yet a further alternative embodiment, the acid-gas removal step uses a physical wash solvent unit that removes the $CO_2$ and some $H_2S$ by contacting the gas with refrigerated methanol, glycol, N-methyl pyrrolidone, propylene carbonate, or glycol ethers such as dimethyl ether of polyethylene glycol.

The resulting $CO_2$-depleted gas stream 512, which may be described as a methane-enriched purified natural gas stream, is split into two portions; a first portion 514 is combined with a higher hydrocarbon stream 516 and the combined stream fed via line 518 though coils in a fired heater 520 fuelled by natural gas and/or higher hydrocarbon, where it is heated to a temperature about 110° C. From fired heater 520 the gas is passed via line 522 to a desulphuriser vessel 524 containing a fixed bed of a particulate zinc oxide desulphurisation absorbent 526 that removes hydrogen sulphide present in the gas. The resulting desulphurised natural gas stream is passed from the desulphuriser vessel 524 vial line 528, mixed with a hydrogen stream in line 529 and the mixture fed to a saturator 530 where it is contacted with a stream of hot water/steam at a temperature about 190° C. at a pressure about 10 bar abs. The saturated hydrocarbon/steam mixture is then fed at a temperature about 180° C. via line 532 to the inlet of a reformer vessel 534 containing a supported ruthenium steam reforming catalyst 536. The steam reforming reactions take place adiabatically as the hydrocarbon-steam mixture passes through the catalyst. The hot reformed gas mixture is cooled in a heat exchanger 538 and one or more further heat exchangers (not shown) to below the dew point to generate a condensate/gas mixture, which is fed via line 540 to a first separator 542. The condensed liquids are recovered via line 544 and the gases fed via line 546 to a water-cooled heat exchanger 548 where they are further cooled and then to a second separator 550. The remaining condensate is recovered from the separator 550 via line 552 and combined with the condensate stream 544 from the first separator.

The combined condensate streams are fed to a condensate stripper 554. A water feed stream 556 from the condensate stripper is mixed with make-up boiler feed water 558 and the combined water fed to the heat exchanger 538 where it is heated in indirect heat exchange with the reformed gas mixture. A heated water/steam stream 560 from the heat exchanger 538 is combined with a pumped re-circulated hot water stream 562 from the saturator 530 and the combined water/steam mixture is further heated by passing it through coils in the fired heater 520. The heated water/steam stream is fed to the saturator 530 from the fired heater 520 via line 564.

The de-watered reformed gas mixture recovered from the second separator 550 is fed via line 508 to the purified natural gas stream 506 to form the gas mixture fed to the acid gas recovery unit (AGRU) 510.

The remaining portion of the methane-enriched natural gas stream 512 is fed via line 566 to a drier vessel 568 where it contacts a zeolitic molecular sieve that acts as a desiccant to remove water. The dried gas stream is then fed to a liquefaction and fractionation unit, where it is first cooled to between −20 and −40° C. in heat exchanger 570, which causes higher hydrocarbons to condense, and the resulting stream fed to a first fractionation column 572 where the higher hydrocarbons are separated from a methane-rich stream. The condensates include heavy components such as benzene, cyclohexane, some propane and butane and C5+ paraffins, and also some ethane and dissolved methane. The light fraction 574 from the top of the column 572 is further cooled in heat exchanger 576 and condensed liquids separated in separator 578. These liquids are returned to the column 572 via line 580. The separated gas from separator 578 is then further cooled in heat exchanger 582 to form a liquefied natural gas 584. The higher hydrocarbon stream recovered from column 572 is fed via line 586 to a second fractionation column 588 (de-ethaniser) operated to recover an ethane-rich stream 590. The ethane stream 590 is vapourised in a vapouriser (not shown) and sent via line 516 to be combined with the first portion of the methane-rich stream 514 from the AGRU 310.

The mixed stream 592 recovered from the bottom of the second fractionation column 588 is sent to a third column 594 (de-propaniser) where a propane-rich stream 596 is recovered. The mixed stream 598 recovered from the bottom of the third fractionation column 594 is sent to a fourth column 600 (de-butaniser) where a butane-rich stream 602, and condensates stream 604 are recovered. The propane 596, butane 602 and condensates 604 obtained from the de-propaniser 594 and debutaniser 600 respectively may be sent for storage. If desired, a portion of these streams (shown by dotted lines) may be combined with the ethane stream 590 and sent via line 516 to be used as part of the natural gas stream.

It will be understood that the above described liquefaction and fractionation unit may also be used in the embodiment depicted in FIG. 4.

Furthermore, if desired, between drier 568 and heat exchanger 570, the purified, $CO_2$-depleted and dried methane-enriched natural gas stream may be passed through a preliminary separation unit (not shown) containing a membrane that separates a portion of the higher hydrocarbon from the natural gas, thereby forming a gaseous higher hydrocarbon stream, which is then fed to the higher hydrocarbon vapouriser.

In a further alternative embodiment, a portion of the purified natural gas stream 506 from the purification vessel 502 may be combined with the higher hydrocarbon stream 516 to form part of the natural gas stream fed to the reforming process. Moreover, it will be understood that where the mercury content of the natural gas feed is negligible, purification vessel 502 and sorbent 504 may be omitted. Similarly, where the $CO_2$ content of the natural gas is negligible, the purified natural gas stream 506 may be directly combined with the higher hydrocarbon stream 516.

EXAMPLES

The process of the present invention may be applied to so-called "rich" or "lean" natural gases. For example, natural gases that may be subjected to catalytic de-enrichment according to the present invention may have the following compositions:

1) LNG ex Marsa El Braga Libya (Wobbe 53.26 MJ/m$^3$)
Methane 83.68%
Ethane 11.73%
Propanes 3.51%
Butanes 0.28
Nitrogen 0.8%

2) LNG ex ADGAS UAE (Wobbe 53.48 MJ/m$^3$)
Methane 84.0%
Ethane 14.0%
Propanes 1.0%
Butanes 0.9%
Nitrogen 0.1%

With this case, where the process is operated at a steam: carbon ratio (being the steam to higher hydrocarbon carbon ratio) of 2:1, the reformer inlet temperatures and reforming pressures are desirably as follows;

| Inlet Temperature (° C.) | 150 | 230 | 250 |
|---|---|---|---|
| Pressure (bar abs.) | 10 | 70 | 100 |

3) Natural gas
Methane 70%
Ethane 15.0%
Propanes 5.0%
Butanes 5.0%
Pentanes 2.0%
Nitrogen 3.0%

With this case, where the process is operated at a steam:carbon ratio (being the steam to higher hydrocarbon carbon ratio) of 2:1, the reformer inlet temperatures and reforming pressures are desirably as follows;

| Inlet Temperature (° C.) | 160 | 250 |
|---|---|---|
| Pressure (bar abs.) | 10 | 70 |

Alternatively the production of liquefied natural gas may be increased by conversion of the natural gas liquids into methane. The following table shows the potential increase in LNG production using the process of the present invention.

| | Gas Composition (% vol) | | | | Potential Increase | |
|---|---|---|---|---|---|---|
| Example | C1 | C2 | C3 | C4 | C1 Amount | C1 % Increase |
| 1 | 100 | — | — | — | 100 | 0 |
| 2 | 95 | 5 | — | — | 104 | 9 |
| 3 | 90 | 5 | 3 | 2 | 113 | 26 |
| 4 | 85 | 10 | 5 | — | 115 | 35 |

The invention claimed is:

1. A process for treating a natural gas stream containing methane and one or more higher hydrocarbons comprising the steps of:
   (i) forming a mixture of natural gas, steam and hydrogen by mixing at least a portion of the natural gas stream with steam at a steam:carbon ratio in the range 0.2:1 to 3:1 based on the one or more higher hydrocarbons carbon, and hydrogen at a concentration up to 5% vol,
   (ii) passing the mixture adiabatically over a supported precious metal reforming catalyst at an inlet temperature in the range 130-300° C. to generate a reformed gas mixture comprising methane, steam, carbon dioxide, carbon monoxide and hydrogen,
   (iii) cooling the reformed gas mixture to below the dew point to condense water and removing the condensate to provide a de-watered reformed gas mixture, and
   (iv) passing the de-watered reformed gas mixture through an acid gas recovery unit to remove carbon dioxide and at least a portion of the hydrogen and carbon monoxide, thereby generating a methane stream.

2. A process according to claim 1 wherein the natural gas stream is processed in an offshore processing facility selected from a fixed off-shore facility or a floating off-shore facility.

3. A process according to claim 1 wherein the amount of methane in the natural gas stream is in the range 50 to 95% by volume.

4. A process according to claim 1 wherein the natural gas stream is selected from the group consisting of an associated gas, shale gas, tight sand gas, coal bed methane, or a synthetic natural gas mixture comprising methane and one or more higher hydrocarbons.

5. A process according to claim 1 further comprising a step of liquefying the methane stream in a LNG liquefaction unit wherein the natural gas stream is a natural gas containing one or more higher hydrocarbons which is fed to the reforming stage so that the natural gas liquefaction step processes only methane to LNG and no liquefied higher hydrocarbons are produced.

6. A process according to claim 1 wherein the natural gas stream comprises a portion of a natural gas feed stream and a remaining portion is mixed with the de-watered reformed gas mixture or methane stream to produce a methane-enriched natural gas stream.

7. A process according to claim 6 further comprising a step of liquefying the methane enriched natural gas stream in a LNG liquefaction unit.

8. A process according to claim 7 wherein one or more of higher hydrocarbon streams separated in the liquefaction unit is fed to the reformer as part of the natural gas stream.

9. A process according to claim 1 wherein the natural gas stream comprises a portion of a methane-enriched natural gas and one or more higher hydrocarbons, said methane-enriched natural gas produced by mixing a natural gas feedstock with the de-watered reformed gas mixture, feeding the mixture to the acid gas recovery unit and recovering the methane-enriched natural gas therefrom, and said one or more higher hydrocarbons is produced by liquefying and fractionating a further portion of said methane-enriched natural gas.

10. A process according to claim 1 comprising purifying the natural gas stream to remove mercury upstream of mixing the natural gas stream with steam by passing the natural gas stream through a purification unit containing a purification material suitable for removing mercury.

11. A process according to claim 1 comprising purifying the natural gas stream to remove sulphur compounds upstream of mixing the natural gas stream with steam by passing the natural gas stream through a purification unit containing a purification material suitable for removing sulphur compounds.

12. A process according to claim 1 wherein the steam is mixed with the natural gas stream using a saturator.

13. A process according to claim 1 wherein the inlet temperature of the natural gas/steam mixture fed to the reforming catalyst is in the range 150-275° C.

14. A process according to claim 1 wherein the pressure of the natural gas/steam mixture fed to the reforming catalyst is in the range 10-100 bar abs.

15. A process according to claim 1 wherein hydrogen is Included in the natural gas/steam mixture at a concentration up to 3% vol.

16. A process according to claim 1 wherein the supported precious metal reforming catalyst comprises one or more of Pt, Pd, Ir, Rh or Ru in the range 0.1-10% by weight.

17. A process according to claim 1 comprising exchanging heat, in one or more heat exchangers, between the reformed gas mixture and water to generate at least a portion of the steam used in the reforming step.

18. A process according to claim 1 wherein at least a portion of the process condensate is used to generate at least a portion of the steam mixed with the natural gas stream.

19. A process according to claim 1 wherein the acid gas recovery unit comprises a membrane or a physical wash solvent system or an amine wash system.

20. A process according to claim 1 comprising drying the methane-stream stream using a drying unit.

* * * * *